(12) United States Patent
Soloveichik et al.

(10) Patent No.: US 7,084,291 B2
(45) Date of Patent: Aug. 1, 2006

(54) WATER RESISTANT CATALYST FOR THE PRODUCTION OF DIARYL CARBONATES VIA THE DIRECT CARBONYLATION OF PHENOLIC COMPOUNDS

(75) Inventors: Grigorii Lev Soloveichik, Latham, NY (US); Timothy Leigh Chuck, Canajoharie, NY (US); Kirill Vladimirovich Shalyaev, Waukesha, WI (US); Eric James Pressman, East Greenbush, NY (US); Peter John Bonitatebus, Jr., Guilderland, NY (US)

(73) Assignee: General Electric Company, Niskayuna, NY (US)

( * ) Notice: Subject to any disclaimer, the term of this patent is extended or adjusted under 35 U.S.C. 154(b) by 266 days.

(21) Appl. No.: 10/687,411

(22) Filed: Oct. 15, 2003

(65) Prior Publication Data

US 2005/0085656 A1    Apr. 21, 2005

(51) Int. Cl.
*C07C 69/96* (2006.01)
(52) U.S. Cl. .................................................... 558/274
(58) Field of Classification Search ................. 558/274
See application file for complete search history.

(56) References Cited

U.S. PATENT DOCUMENTS

| 5,380,907 A | 1/1995 | Mizukami et al. |
| 5,856,554 A | 1/1999 | Buysch et al. |
| 6,114,564 A | 9/2000 | Pressman et al. |
| 6,365,538 B1 | 4/2002 | Shalyaev et al. |
| 6,423,863 B1 * | 7/2002 | Pressman .................. 558/274 |
| 6,548,445 B1 | 4/2003 | Buysch et al. |
| 6,566,229 B1 | 5/2003 | Spivack et al. |
| 6,566,295 B1 | 5/2003 | Shalyaev et al. |
| 6,852,872 B1 * | 2/2005 | Reisinger et al. ........... 558/274 |

OTHER PUBLICATIONS

Copending U.S. Appl. No. 09/822,531, filed Mar. 30, 2001, by Eric James Pressman et al., entitled "Method For Producing Aromatic Carbonates".

* cited by examiner

*Primary Examiner*—Johann Richter
*Assistant Examiner*—Ebenezer Sackey
(74) *Attorney, Agent, or Firm*—Andrew J. Caruso; William E. Powell, III

(57) ABSTRACT

A method of increasing the amount of diphenylcarbonate produced per amount of catalyst consumed in a phenol carbonylation process is described. Phenolic carbonylation produces water as a reaction product which reduces the turnover number (TON) of the catalyst. A mixture of a phenolic precursor, a base containing catalyst and co-catalyst components and at least one chemical additive comprising a halide or hydroxide of alkali metal or alkaline earth metal when carbonylated together under specific conditions increases the turnover number (TON) and water resistivity of a palladium catalyst. The metal halide likely makes the catalyst less susceptible to degradation by water hence increasing the reaction yield per weight of catalyst consumed.

28 Claims, No Drawings

WATER RESISTANT CATALYST FOR THE PRODUCTION OF DIARYL CARBONATES VIA THE DIRECT CARBONYLATION OF PHENOLIC COMPOUNDS

BACKGROUND OF THE INVENTION

This invention relates to a method for making diaryl carbonate using a water resistant catalyst to effect the direct carbonylation of a phenolic compound (the "phenolic precursor") to a diaryl carbonate. More particularly, the method relates to increasing the turnover number (TON) of the catalyst employed in the carbonylation reaction by making it less susceptible to degradation by the water generated as a by-product during the carbonylation reaction. The turnover number (TON) is a measure of the efficiency of the carbonylation catalyst. TON may be defined as the number of moles of a product diaryl carbonate produced per mole of catalyst employed.

Water removal techniques in phenol carbonylation reactions have been the subject of intense research in an effort to increase the useful life and TON of water-sensitive carbonylation catalysts. Water tends to poison Group 9 metal carbonylation catalysts typically employed during the carbonylation of phenolic compounds to diaryl carbonates, thereby increasing the overall cost of production.

Providing a means for water removal in carbonylation reactions has been shown to provide increased catalyst turnover numbers. In some instances carbonylation catalyst turnover numbers as high as about 6000 have been achieved when a means for water removal has been provided. Efficient water removal is expected to provide a manifold increase in the useful life of the carbonylation catalyst.

Current methods of overcoming the effects of water generated during the production of diaryl carbonates include water removal by molecular sieves, and water entrainment out of the reaction mixture by evaporation. Water removal using molecular sieves may yield high TONs but the use of molecular sieves is marked by disadvantages such as cost, fines production, handling and regeneration difficulties, and the like.

The present invention provides an alternate approach to increasing the carbonylation catalyst turnover number by making the carbonylation catalyst water resistant.

Since overcoming the negative effects of water produced in the carbonylation reaction using molecular sieves, evaporative removal of water from the carbonylation reaction mixture, and like methods entails added costs (e.g. cost of molecular sieves or the increased investment costs required to develop an evaporation column), it would be desirable to provide a method for making diaryl carbonates which benefited from the use of a water resistant carbonylation catalyst. The present invention provides a method for the carbonylation of phenolic compounds which employs one or more chemical agents which improve the stability of the noble metal carbonylation catalysts typically employed during the carbonylation of phenolic compounds to diaryl carbonates. Due to this enhanced resistance to the deleterious effects of water, the method of the present invention achieves more efficient use of the noble metal carbonylation catalysts employed. This and other purposes of the present invention are disclosed in detail herein.

BRIEF SUMMARY OF THE INVENTION

The present invention relates to a method for the preparation of diaryl carbonates. In one aspect, the method of the present invention provides diaryl carbonates by contacting in a reaction mixture a phenolic precursor with carbon monoxide and oxygen in the presence of a carbonylation catalyst comprising palladium or a compound thereof, a co-catalyst, a base, a halide source, and a chemical additive for increasing the amount of diaryl carbonate produced per unit of the carbonylation catalyst employed. The chemical additive comprises a salt of magnesium or lithium, or a combination thereof, said chemical additive being present in an amount corresponding to at least 25 equivalents of lithium, magnesium, or a combination thereof relative to an amount of palladium present in the carbonylation catalyst.

In one aspect, the present invention provides a method of increasing the useful life and turnover number (TON) of the noble metal catalyst used in the production of diphenylcarbonate via the direct carbonylation of phenol, said method comprising the addition of one or more of magnesium or lithium salts to the reaction mixture during the carbonylation of phenol to diphenylcarbonate in the presence of a palladium-copper-titanium catalyst-cocatalyst combination In another aspect, the present invention relates to the development of a new process of limiting the deleterious effects of water produced during phenol carbonylation.

In a fourth aspect, the present invention relates to the development of a water-resistant catalyst system to aid efficient carbonylation of phenol to diphenylcarbonate.

DETAILED DESCRIPTION OF THE INVENTION

The present invention may be understood more readily by reference to the following detailed description of preferred embodiments of the invention and the examples included herein. In this specification and in the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

The "Group 9 metals" consist of iron, ruthenium, osmium, cobalt, rhenium, iridium, nickel, palladium, and platinum.

The concentration of magnesium or lithium species in terms of equivalents versus palladium generally refers to the molecular concentration of respective species. It refers to ionic concentrations when thus specifically stated.

Aromatic hydroxy compounds which may be used as phenolic precursors in the practice of the present invention include aromatic mono- or polyhydroxy compounds, such as phenol, p-cresol, o-cresol, m-cresol, xylenol, resorcinol, hydroquinone, bisphenol A, 4-fluorophenol, methyl salicylate, and mixtures thereof. Aromatic organic monohydroxy compounds are preferred, with phenol being more preferred. The examples of aromatic hydroxy compounds provided above are for illustrative purposes and are in no way intended to limit the scope of the applicability of the method of the present invention. Thus, nearly any aromatic hydroxy compound may be employed according to the method of the present invention.

In various preferred embodiments, the carbonylation catalyst system contains at least one constituent from the Group 9 metals or a compound thereof. A preferred Group 9 constituent is an effective amount of a palladium source. In various embodiments, the palladium source may be in elemental form, or it may be employed as a palladium compound. Accordingly, palladium black or elemental palladium deposited on carbon may be used as well as palladium halides, nitrates, carboxylates, oxides and palladium complexes containing carbon monoxide, amines, phosphines or olefins. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium (II) salts of organic acids, including carboxylates with $C_2$–$C_6$ aliphatic acids. Palladium(II) acetylacetonate is also a suitable palladium source. For purposes of the present invention the terms "palladium(II) acetylacetonate" and "palladium acetylacetonate" are interchangeable and refer to the same chemical species. Preferably, the amount of Group 9 metal source employed should be sufficient to provide about 1 mole of metal per 800–10,000 moles of aromatic hydroxy compound. More preferably, the proportion of Group 9 metal source employed should be sufficient to provide about 1 mole of metal per 2,000–5,000 moles of aromatic hydroxy compound.

The formation of diaryl carbonates in a carbonylation reaction can be accompanied by the formation of by-products, such as bisphenols, in varying proportions. In order to increase selectivity to diaryl carbonate, various organic co-catalysts may be incorporated in the carbonylation catalyst system. Depending on the application, suitable organic co-catalysts may include various phosphine, quinone, terpyridine, phenanthroline, quinoline and isoquinoline compounds and their derivatives, such as 2,2':6',2-terpyridine; 4'-methylthio-2,2':6',2-terpyridine; 2,2':6', 2-terpyridine N-oxide; 1,10-phenanthroline; 2,4,7,8-tetramethyl-1,10-phenanthroline; 4,7-diphenyl-1,10-phenanthroline; and 3,4, 7,8-tetramethyl-1,10-phenanthroline.

The carbonylation catalyst system includes a catalytic amount of an inorganic co-catalyst (IOCC) containing copper. In addition to copper (or titanium) per se, it has been discovered that certain IOCC combinations can effectively catalyze the carbonylation reaction. Such IOCC combinations, provided the additional IOCC does not deactivate (i.e. "poison") the original IOCC combination, may comprise ytterbium, yttrium, europium, lead, zinc, manganese, cobalt, nickel, zirconium, bismuth, iridium, ruthenium, rhodium, and chromium. Further IOCC combinations include ytterbium and copper; ytterbium, copper, and titanium; ytterbium, copper, and iron; ytterbium and cerium; ytterbium and manganese; ytterbium, manganese, and europium; ytterbium, manganese, and bismuth; ytterbium and europium;. ytterbium and nickel; ytterbium and bismuth; ytterbium and zinc; ytterbium and iron; ytterbium and cobalt; ytterbium and iridium; ytterbium and ruthenium; ytterbium and rhodium; and ytterbium and chromium.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include those known in the art as ligands for the IOCC metals of the present invention. Examples include, but are not limited to, acetylacetone, benzoylacetone, dibenzoylmethane, diisobutyrylmethane, 2,2-dimethylheptane-3,5-dione; 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). An IOCC may be used in its elemental form if sufficient reactive surface area can be provided.

IOCC's are included in the carbonylation catalyst system in catalytic amounts. In this context a "catalytic amount" is an amount of IOCC (or combination of IOCC's) that increases the number of moles of aromatic carbonate produced per mole of Group 9 metal utilized; increases the number of moles of aromatic carbonate produced per mole of halide utilized; or increases selectivity toward aromatic carbonate production beyond that obtained in the absence of the IOCC (or combination of IOCC's). Optimum amounts of an IOCC in a given application will depend on various factors, such as the identity of reactants and reaction conditions. Additional IOCC's may be used in the carbonylation catalyst system, provided the additional IOCC does not deactivate (i.e. "poison") the original IOCC.

The carbonylation reaction can be carried out in a batch reactor or a continuous reactor system. Due in part to the low solubility of carbon monoxide in organic hydroxy compounds, such as phenol, it is preferable that the reactor vessel be pressurized. In preferred embodiments, gas can be supplied to the reactor vessel in proportions of between about 2 and about 50 mole percent oxygen, with the balance being carbon monoxide. Additional gases may be present in amounts that do not deleteriously affect the carbonylation reaction. The gases may be introduced separately or as a mixture. A total pressure in the range of between about 10 and about 250 atmospheres is preferred. Although in one aspect the method of the present invention provides a means for reducing or eliminating the need for drying agents, drying agents, typically molecular sieves, may be present in the reaction vessel and where present such drying agents may confer yet additional advantages. Reaction temperatures in the range of between about 60° C. and about 150° C. are preferred. Gas sparging or mixing can be used to aid the reaction.

In the practice of one embodiment of the invention, the constituents of the carbonylation reaction mixture comprising the hydroxy aromatic compound to be carbonylated, the catalyst, co-catalyst, base, halide source, and chemical additive for increasing the amount of diaryl carbonate produced per unit of the carbonylation catalyst are charged to the reactor system. The reactor system typically comprises a jacketed, heated, sealable, reaction vessel, which may be operated at pressures higher than one atmosphere, and a condenser. Typically heating is effected by passage of heated oil through the reaction vessel jacket. The system is sealed. Carbon monoxide and oxygen are introduced into the reaction vessel until a preferred pressure (as previously defined) is achieved. Circulation of condenser water is initiated, and the temperature of the reaction vessel is raised to a desired operating temperature. The pressure in reaction vessel can be controlled by, for example, the combination of reducing pressure regulator and back pressure regulator. Upon reaching the desired reactor temperature, aliquots are taken to monitor the progress of the carbonylation reaction.

In one aspect the present invention provides a means of increasing the turnover number (TON) of a Pd—Cu—Ti catalyst used in the production of diphenylcarbonate via the direct carbonylation of phenol. Most catalytic systems for direct phenol carbonylation to diphenylcarbonate perform unsatisfactorily without a water removal mechanism. Representative catalyst systems and water removal techniques are known. (See, for example, U.S. Pat. No. 6,365,538.) Water is produced in the course of the carbonylation reaction (1 mole of water per mole of diphenylcarbonate) and may inhibit or even completely poison the catalyst. In instances in which a palladium catalyst is employed, catalyst performance measured by Pd turnover number (TON). Typically catalyst performance, as measured by TON, when the carbonylation reaction is conducted without water removal is only about 50 to about 70 percent of that observed when steps are taken to effect water removal.

In the instant invention it has been discovered that a chemical additive comprising a salt of magnesium or lithium, or a combination thereof, in an amount corresponding to at least 25 equivalents of lithium, magnesium, or a combination thereof relative to an amount of amount of at least Group 9 metal carbonylation catalyst present in the carbonylation reaction mixture effectively reduces the negative effects of water on catalyst performance. In one embodiment of the present invention the carbonylation catalyst is palladium or a compound thereof, for example palladium acetyl acetonate. While it has been discovered that the chemical additive comprising a salt of magnesium or lithium must be present in a minimum amount corresponding to about 25 equivalents of lithium, magnesium, or a combination thereof relative to the carbonylation catalyst, it has been found as well that beyond about 950 equivalents of lithium, magnesium, or a combination thereof relative to an of the amount of carbonylation catalyst present, the effectiveness of the method is greatly reduced. Thus in preferred embodiments of the present invention the amount of chemical additive employed is between about 25 and about 950, preferably between about 100 and about 800 and still more preferably between about 200 and about 650 equivalents of lithium, magnesium, or a combination thereof relative to the amount of the carbonylation catalyst. Preferred salts of magnesium include magnesium bromide ($MgBr_2$), magnesium bromide chloride (MgBrCl), magnesium acetate ($Mg(OAc)_2$), magnesium hydroxide ($Mg(OH)_2$), and the like. Preferred salts of lithium include lithium bromide (LiBr), lithium acetate (LiOAc), lithium chloride (LiCl), and lithium hydroxide (LiOH). The chemical additive may be a single salt of lithium or magnesium, a plurality of lithium or magnesium salts, or a mixture comprising one or more salts of each of lithium and magnesium. As noted, when added in specific amounts to the reaction mixture in presence of a palladium catalyst and a copper-titanium co-catalyst the salts of magnesium and lithium have been found to increase the turnover number of the catalyst. This increase in TON is believed to be due to the catalyst's increased resistance to the effects of water, referred to here as "water resistivity". Water resistivity is defined herein as the ratio of catalyst turnover number (TON) measured for a reaction run without having taken steps to effect water removal, to the turnover number obtained in the presence of molecular sieves. In the examples provided with the description of the present invention water resistivity values in excess of 1.0 are observed and are shown to be the result of the use of magnesium and lithium salt chemical additives. It should be noted that in a large number of instances falling within the scope of the present invention, water resistivity values of less than 1.0 are also observed. It should be stressed, however, that catalyst performance in such systems is still generally superior to systems employing neither known water removal techniques (e.g. the use of molecular sieves) nor the magnesium and lithium salt chemical additives used according to the method of the method of the present invention.

As noted, the method of the present invention employs a halide source in an amount corresponding to between about 25 and about 1000, preferably about 50 and about 800, and still more preferably about 100 and about 500 equivalents of halide source per mole of Group 9 metal catalyst employed. Typically the halide source comprises at least one alkali metal or alkaline earth metal halide and the Group 9 metal catalyst is palladium or a compound thereof. Typically alkali metal or alkaline earth metal bromides are preferred. In certain embodiments of the present invention the halide source comprises at least one quaternary ammonium or quaternary phosphonium halide. Suitable quaternary ammonium halides include tetramethylammonium bromide, tetrabutylammonium bromide, tetramethylammonium chloride and the like. Suitable quaternary phosphonium halides include tetramethylphosphonium bromide, tetrabutylphosphonium bromide, and the like.

As noted, the method of the present invention is carried out in the presence of at least one base. Typically, the base is present in an amount corresponding to between about 75 and about 1000, preferably between about 100 and about 900, and still more preferably between about 200 and about 800 equivalents of base per mole of Group 9 metal catalyst employed. Bases which may be used according to the method of the present invention include inorganic bases, organic bases, and mixtures thereof. Inorganic bases typically employed include metal hydroxides such as sodium hydroxide (NaOH), potassium hydroxide (KOH). It should be noted that the base employed may serve a dual function, as where the base employed also comprises a salt of lithium or magnesium. In such an instance the salt of lithium or magnesium serves the dual role as "base" and "chemical additive". For example were the base employed is lithium hydroxide (LiOH) it also constitutes a chemical additive comprising a salt of lithium which acts to enhance the resistance of the Group 9 metal catalyst to the effects of water generated during the carbonylation reaction.

As noted the base may be either an inorganic base or an organic base. Where the base is an inorganic base it has been found necessary to include an "activating solvent" in the carbonylation reaction mixture in order to achieve satisfactory results. Activating solvents suitable for use according to the method of the present invention include ethers, polyethers, nitriles, sulfones, amides, alkyl carbonates, and mixtures thereof. Preferred activating solvents include ethers such as tetrahydrofuran, and polyethers such as diglyme, triglyme, tetraglyme, crown ethers, and mixtures thereof. Typically, the activating solvent is present in an amount corresponding to between about 1 and about 90, preferably between about 2 and about 50, and still more preferably between about 5 and about 15 percent by weight of the carbonylation reaction mixture at the outset of the reaction.

In embodiments in which the base is an organic base, there is no requirement that an activating solvent be present in the carbonylation reaction mixture. Thus, when an organic base is present, the presence of an activating solvent is optional. Organic bases suitable for use according to the method of the present invention include quaternary ammonium hydroxides, quaternary phosphonium hydroxides, tertiary amines, and mixtures thereof. Quaternary ammonium hydroxides are illustrated by tetramethylammonium hydrox ide and tetrabutylammonium hydroxide. Quaternary phosphonium hydroxides are illustrated by tetramethylphosphonium hydroxide and tetrabutylphosphonium hydroxide. For the purposes of this disclosure tertiary amines are defined as comprising both aliphatic tertiary trialkylamines such as triethylamine and cycloaliphatic tertiary amines diazabicyclooctane (DABCO), as well as aromatic tertiary amines such as pyridine and 4-N,N-dimethyaminopyridine. In one aspect of the present invention it has been discovered that tertiary amine bases perform optimally when the tertiary amine base is an amine hydrate. For convenience, an amine hydrate is defined herein as an amine comprising water in an amount corresponding to between about 0.2 moles of water per mole of amine, to about 2 moles of water per mole of amnine. Amine hydrates are effectively employed by adding the anhydrous amine and the requisite amount of water (about 0.2 to about 2 equivalents of water based on the amine) to the carbonylation reaction mixture. In one embodiment of the present invention the organic base comprises at least one trialkylamine hydrate, for example triethylamine hydrate. It should be noted that when the organic base is a quaternary ammonium hydroxide or a quaternary phosphonium hydroxide there is no need to add additional water to the reaction mixture in order for the organic base to be optimally effective.

EXAMPLES

The following examples are set forth to provide those of ordinary skill in the art with a detailed description of how the methods claimed herein are carried out and evaluated, and are not intended to limit the scope of what the inventors regard as their invention.

General Experimental

Preparation of Diphenylcarbonate: Effect on Turnover Number (TON)

Catalyst system activity was studied using a 17-pack reactor system. Seventeen 3-dram vials were charged each with about 5.5 g phenol, about 0.4 g tetraglyme containing all catalyst components (copper(II) acetylacetonate, titanium(IV) oxide acetylacetonate, and various combinations of lithium bromide, lithium chloride lithium hydroxide, sodium bromide, sodium hydroxide and magnesium bromide in the amounts as shown in Tables 1 and Table 3) along with Pd acetylacetonate (0.0028 g; 0.009 mmol; 14 ppm). For instance, in Table 1 Control-1 and Control-2, 250 equivalents vs Pd of NaBr, 700 equivalents vs Pd of NaOH and 7 wt % of tetraglyme were introduced into the reaction mixture. The experiments represented in Tables 1–3 were performed using the amounts of the various reactants listed in the tables. In selected experiments molecular sieves (1/16" pellets) were present in the reaction mixture. Each vial was equipped with a magnetic stirbar and sealed with a Teflon lined cap having a predrilled hole having a diameter of about 1 mm. The vials were positioned in an aluminum block, which was placed in a 1 gallon pressurized reactor equipped with a stir shaft. The reactor vessel was sealed and pressurized to 1300 psi with a 9% mixture of oxygen in carbon monoxide. The reactor was heated to 100° C. over 10 minutes. A large magnet was mounted on the stir shaft of the reactor to provide stirring in the individual reaction vials. The reaction temperature was maintained at 100° C. for 2 hours. After cooling and depressurization, reaction aliquots were collected and analyzed by high performance liquid chromatography (HPLC) for diphenylcarbonate, phenol and bromophenols content. The palladium turnover number (TON) was calculated on the basis of moles of diphenylcarbonate produced per mole of palladium introduced. Selectivity was calculated on the basis of 0.5 moles of diphenylcarbonate produced per mole of phenol consumed. Water resistivity was measured as a ratio of palladium TON obtained without water removal to palladium TON obtained in the presence of molecular sieves.

Preparation of Diphenylcarbonate: Increase in Water Resistivity

In Table 1 $MgBr_2$, NaBr and NaOH levels are shown to affect catalyst performance and selectivity, so their most effective combination determines the most desirable process outcome. The effect of the magnesium salt on water resistivity of the catalyst has been evaluated and confirmed in larger scale reactions (presented in Table 2). The water resistivity coefficient for the Pd—Cu—Ti—NaBr—NaOH-tetraglyme package, measured as the ratio of Pd TON obtained without water removal (without molecular sieves) to Pd TON obtained in the presence of molecular sieves, depends on the reaction time and was in the range 0.52–0.67 for 2.5 hour reaction times (Control-11 in Table 2). The addition of $MgBr_2$ results in an increase in the water resistivity value to 0.8 under similar conditions (Example 13 in Table 2). In certain cases, (Table 3) a water resistivity of 1.08 was obtained using 250 equivalents vs Pd of NaBr and 350 equivalents vs Pd of LiOH and catalyst to yield a TON of 5667 and a water resistivity of 1.08 (Example 26, Table 3). Similarly, 250 equivalents vs Pd of LiBr and 100 equivalents vs Pd of LiOH when added to the phenolic precursor and catalyst, yielded a TON of 5501 and a water resistivity of 1.08 (Example 32, Table 3). The data in Table 3 demonstrate the beneficial effect of total lithium concentration on water resistivity and illustrate a dual role use of lithium hydoxide; as a base and as a chemical additive conferring enhanced water resistivity. The experimental data in Table 3 reveal that both TON and water resistivity values are sensitive to lithium concentration. In these instances, the performance of the water resistant catalyst system of the present invention is comparable to, or in some instances exceeds the performance of the same catalyst in the presence of molecular sieves. In other words, the water resistant catalyst systems of the present invention do not require the use of molecular sieves to achieve high catalyst TONs.

Preparation of Diphenylcarbonate: Use of Organic Bases (Table 4)

Experiments were carried out (Table 4) in which the inorganic base employed in the experiments represented in Tables 1–3 was replaced by an organic base. The data demonstrate that tetraalkylammonium hydroxides (Examples 40–43) make suitable bases for use according to the method of the present invention. The data further reveal that tertiary amines and in particular triakylamines are also effective, particularly when the amine is present as its hydrated form (amine hydrate). For convenience, an amine hydrate is defined herein as an amine comprising water in an amount corresponding to between about 0.2 moles of water per mole of amine, to about 2 moles of water per mole of amine. Surprisingly, the presence of the these low levels of water which are required for optimal performance of catalyst systems comprising a tertiary amine bases does necessarily negatively affect the overall catalyst performance.

TABLE 1

DPC production and reaction selectivity as a function of the catalytic package components in the system Pd—Cu—Ti-magnesium bromide-inorganic base in 17-pack reactor[a]

| No. | MgBr₂ | NaBr | NaOH | Sieves | Pd TON[b] | Selectivity, %[c] | Water resistivity[d] |
|---|---|---|---|---|---|---|---|
| Control-1 | — | 250 | 700 | yes | 5596 | 74.0 | |
| Control-2 | — | 250 | 700 | no | 3711 | 73.0 | 0.66 |
| 3 | 100 | — | 750 | no | 4814 | 70.6 | |
| 4 | 100 | 225 | 500 | yes | 5887 | 84.5 | |
| 5 | 100 | 225 | 500 | no | 5108 | 80.4 | 0.87 |
| 6 | 25 | 50 | 600 | no | 3925 | 54.8 | |
| 7 | 100 | 50 | 300 | no | 6184 | 76.9 | |
| 8 | 100 | 225 | 300 | no | 6069 | 75.3 | |
| 9 | 150 | 225 | 600 | no | 6221 | 73.4 | |
| 10* | 100 | — | 400 | No | 0 | — | — |

[a]Reaction conditions: Reaction mixture contained 5.3–5.5 g PhOH, Pd as Pd(acac)₂ (15 ppm), Cu(acac)₂ (12 eq. vs. Pd), TiO(acac)₂ (15 eq. vs. Pd), sodium hydroxide in combination with tetraglyme as an activating solvent (7 wt. %), and, optionally, sodium bromide. Gas mixture contained 9% oxygen in CO at 1300 psi; Desiccant = 1 gram 1/16" 3A molecular sieves immersed in reaction mixture. DPC yield was measured after 2 h. Results presented in the table are average of duplicate runs. The procedure for a representative entry is described in the Experimental section.
[b]Pd TON = Palladium turnover number = moles DPC produced/moles Pd charged
[c]Selectivity is calculated as 0.5 moles DPC produced/(moles PhOH charged - moles PhOH remaining)
[d]Water resistivity measured as ratio of Pd TON obtained without water removal to Pd TON obtained in the presence of molecular sieves
*Example 10 was carried out without tetraglyme (i.e. without an activating solvent present)

TABLE 2

DPC production and reaction selectivity as a function of the catalytic package components in the system Pd—Cu—Ti-magnesium bromide-base in batch-batch reactor[a]

| Run | Cu, eq | Ti, eq | MgBr₂ | NaBr | NaOH | Sieves | Pd TON[b] | Selectivity, %[c] | Water resistivity |
|---|---|---|---|---|---|---|---|---|---|
| Control-11 | 13 | 27 | — | 429 | 805 | Yes | 8318 | 78 | |
| Control-12 | 12 | 25 | — | 400 | 750 | No | 4630 | 70 | 0.56 |
| 13 | 12 | 15 | 100 | 225 | 500 | Yes | 9048 | 75 | |
| 14 | 12 | 15 | 100 | 225 | 500 | No | 7170 | 69 | 0.80 |

[a]Reaction conditions: Reaction mixture contained 60–62 g PhOH, Pd as Pd(acac)₂ (15 ppm), Cu(acac)₂ (12 eq. vs. Pd), TiO(acac)₂ (15 eq. vs. Pd), sodium hydroxide, tetraglyme (7 wt. %), and sodium bromide. Gas mixture contained 9% oxygen in CO at 1300–1600 psi; Desiccant = 30 grams 1/16" 3A molecular sieves immersed in reaction mixture. Maximum DPC yield was measured. The procedure for a representative entry is described in the Experimental section.
[b]Pd TON = Palladium turnover number = moles DPC produced/moles Pd charged
[c]Selectivity is calculated as 0.5 moles DPC produced/(moles PhOH charged - moles PhOH remaining)

TABLE 3

DPC production and reaction selectivity as a function of the catalytic package components in the system Pd—Cu—Ti—Li-halide-base in 17-pack reactor[a]

| No. | NaCl, eq[b] | LiCl, eq | NaBr, eq | LiBr, eq | NaOH, eq | LiOH, eq | Li total, eq | Sieves | Pd TON[c] | Selectivity, %[d] | Water resistivity[e] |
|---|---|---|---|---|---|---|---|---|---|---|---|
| Control-15 | 350 | | | | 650 | | 0 | yes | 3715 | 58.3 | |
| Control-16 | 350 | | | | 650 | | 0 | no | 2538 | 66.0 | 0.68 |
| 17 | | 350 | | | 650 | | 350 | yes | 4111 | 51.2 | |
| 18 | | 350 | | | 650 | | 350 | no | 3036 | 47.3 | 0.74 |
| Control-19 | | | 250 | | 700 | | 0 | yes | 5596 | 74.0 | |
| Control-20 | | | 250 | | 700 | | 0 | no | 3711 | 73.0 | 0.66 |
| 21 | | | | 350 | 500 | | 350 | yes | 5649 | 63.6 | |
| 22 | | | | 350 | 500 | | 350 | no | 5517 | 70.2 | 0.98 |
| 23 | | | | 250 | 600 | | 250 | no | 4815 | 78.4 | |
| 24 | | | | 450 | 400 | | 450 | no | 3298 | 80.7 | |
| 25 | | 250 | | | 350 | 350 | yes | 5242 | 66.8 | |
| 26 | | 250 | | | 350 | 350 | no | 5667 | 77.6 | 1.08 |
| 27 | | 350 | | | 500 | 500 | yes | 5192 | 72.3 | |
| 28 | | 350 | | | 500 | 500 | no | 4388 | 78.4 | 0.85 |
| 29 | | | 100 | | 250 | 350 | yes | 3447 | 53.6 | |
| 30 | | | 100 | | 250 | 350 | no | 3325 | 55.2 | 0.96 |

TABLE 3-continued

DPC production and reaction selectivity as a function of the catalytic package components in the system Pd—Cu—Ti—Li-halide-base in 17-pack reactor[a]

| No. | NaCl, eq[b] | LiCl, eq | NaBr, eq | LiBr, eq | NaOH, eq | LiOH, eq | Li total, eq | Sieves | Pd TON[c] | Selectivity, %[d] | Water resistivity[e] |
|---|---|---|---|---|---|---|---|---|---|---|---|
| 31 | | | | 250 | | 100 | 350 | yes | 5091 | 66.6 | |
| 32 | | | | 250 | | 100 | 350 | no | 5501 | 82.1 | 1.08 |
| 33 | | | | 350 | | 500 | 850 | yes | 5668 | 82.7 | |
| 34 | | | | 350 | | 500 | 850 | no | 3906 | 83.7 | 0.69 |
| 35* | | | | 350 | | 500 | 850 | no | 3519 | 80.5 | |
| 36 | | | 400 | 200 | 100 | | 200 | no | 5770 | 80.4 | |
| 37 | | | 200 | 400 | 100 | | 400 | no | 4665 | 70.5 | |

*tetraglyme was replaced by triglyme
[a]Reaction conditions: Reaction mixture contained 5.3–5.5 g PhOH, Pd as Pd(acac)$_2$ (15 ppm), Cu(acac)$_2$ (13 equivalents vs. Pd for chloride systems, 12 eq. for bromide systems), TiO(acac)$_2$ (45 equivalents vs. Pd for chloride systems, 15 eq. for bromide systems), lithium salt and/or hydroxide, sodium salt and/or hydroxide, and tetraglyme or triglyme (7 wt. %). Gas mixture contained 9% oxygen in CO at 1300 psi; Desiccant = 1 gram 1/16" 3A molecular sieves immersed in reaction mixture. DPC yield was measured after 2 h. Results presented in the table are average of duplicate runs. The procedure for a representative entry is described in the Experimental section.
[b]Equivalents vs. Pd
[c]Pd TON = Palladium turnover number = moles DPC produced/moles Pd charged
[d]Selectivity is calculated as 0.5 moles DPC produced/(moles PhOH charged - moles PhOH remaining)
[e]Water resistivity measured as the ratio of Pd TON obtained without water removal to Pd TON obtained in the presence of molecular sieves

TABLE 4

DPC production and reaction selectivity as a function of the catalytic package components in the system Pd—Cu—Ti—MgBr$_2$-organic base in 17-pack reactor[a]

| No. | MgBr$_2$, eq[b] | Base formula | eq | H$_2$O eq | wt. % | Sieves | Pd TON[c] | Selectivity, %[d] | Water resistivity[e] |
|---|---|---|---|---|---|---|---|---|---|
| Control-38 | — | NMe$_4$OH | 400 | — | — | Yes | 4807 | 55.1 | |
| Control-39 | — | NMe$_4$OH | 400 | — | — | No | 3044 | 42.4 | 0.63 |
| 40 | 100 | NMe$_4$OH | 400 | — | — | Yes | 6935 | 72.2 | |
| 41 | 100 | NMe$_4$OH | 400 | — | — | No | 6445 | 69.5 | 0.93 |
| 42 | 100 | NMe$_4$OH | 200 | — | — | No | 3258 | 53.6 | |
| 43 | 25 | NMe$_4$OH | 400 | — | — | No | 4674 | 53.9 | |
| 44 | 100 | NBu$_3$ | 400 | — | — | yes | 0 | n/a | |
| 45 | 100 | NBu$_3$ | 400 | — | — | no | 1685 | 97.1 | |
| 46 | 100 | NEt$_3$ | 200 | — | — | yes | 3648 | 97.5 | |
| 47 | 100 | NEt$_3$ | 200 | — | — | no | 1534 | 86.2 | 0.42 |
| 48 | 100 | NEt$_3$ | 400 | — | — | yes | 2569 | 50.4 | |
| 49 | 100 | NEt$_3$ | 400 | — | — | no | 3818 | 61.8 | 1.49 |
| 50 | 100 | NEt$_3$ | 600 | — | — | yes | 1531 | 72.8 | |
| 51 | 100 | NEt$_3$ | 600 | — | — | no | 2354 | 74.9 | 1.53 |
| 52 | 100 | NEt$_3$ | 400 | 200 | 0.05 | no | 3424 | 76.5 | |
| 53* | 100 | NEt$_3$ | 300 | 400 | 0.1 | no | 4402 | 85.6 | |
| 54* | 125 | NEt$_3$ | 400 | 275 | 0.07 | no | 4798 | 69.7 | |
| 55* | 200 | NEt$_3$ | 500 | 150 | 0.04 | no | 4028 | | |
| 56* | 200 | NEt$_3$ | 300 | 150 | 0.04 | no | 0 | n/a | |
| 57 | 200 | NEt$_3$ | 300 | 650 | 0.16 | no | 0 | n/a | |

[a]Reaction conditions: Reaction mixture contained 5.3–5.5 g PhOH, Pd as Pd(acac)$_2$ (15 ppm), Cu(acac)$_2$ (12 equivalents vs. Pd), TiO(acac)$_2$ (15 equivalents vs. Pd), magnesium bromide, a base and, optionally, water. Gas mixture contained 9% oxygen in CO at 1300 psi; Desiccant = 1 gram 1/16" 3A molecular sieves immersed in reaction mixture. DPC yield was measured after 2 h. Results presented in the table are average of duplicate or single (*) runs. The procedure for a representative entry is described in the Reduction to Practice section.
[b]Equivalents vs. Pd
[c]Pd TON = Palladium turnover number = moles DPC produced/moles Pd charged
[d]Selectivity is calculated as 0.5 moles DPC produced/(moles PhOH charged - moles PhOH remaining)
[e]Water resistivity measured as the ratio of Pd TON obtained without water removal to Pd TON obtained in the presence of molecular sieves The invention has been described in detail with particular reference to preferred embodiments thereof, but it will be understood by those skilled in the art that variations and modifications can be effected within the spirit and scope of the invention.

What is claimed is:

1. A method for making a diaryl carbonate, said method comprising:
    contacting in a reaction mixture an aromatic hydroxy compound with carbon monoxide and oxygen in the presence of a carbonylation catalyst comprising palladium or a compound thereof, a co-catalyst, a base, a halide source, and a chemical additive for increasing the amount of diaryl carbonate produced per unit of the carbonylation catalyst, said chemical additive comprising a salt of magnesium or lithium, or a combination thereof, said chemical additive being present in an amount corresponding to at least 25 equivalents of lithium, magnesium, or a combination thereof relative to an amount of palladium present in the carbonylation catalyst.

2. The method according to claim 1 wherein said palladium catalyst is present as initially palladium acetylacetonate.

3. A method according to claim 1 wherein the co-catalyst comprises copper and titanium.

4. The method according to claim 3 wherein said co-catalyst comprises at least one compound selected from the group consisting of copper compounds, and titanium compounds.

5. A method according to claim 1 wherein said halide source comprises bromide.

6. A method according to claim 5 wherein said halide source comprises lithium bromide, magnesium bromide, or a combination thereof.

7. A method according to claim 1 wherein said reaction mixture further comprises at least one activating solvent.

8. A method according to claim 7 wherein said base is an inorganic base.

9. A method according to claim 7 wherein said activating solvent is selected form the group consisting of ethers, polyethers, nitriles, sulfones, amides, alkyl carbonates, and mixtures thereof.

10. A method according to claim 9 wherein said solvent is a polyether selected from the group consisting of diglyme, triglyme, tetraglyme, crown ethers, and mixtures thereof.

11. A method according to claim 10 wherein said base is lithium hydroxide, sodium hydroxide, potassium hydroxide, or mixtures thereof.

12. A method according to claim 11 wherein said base is lithium hydroxide.

13. The method according to claim 1 wherein said chemical additive is present in an amount corresponding to between 25 equivalents and about 950 equivalents of lithium, magnesium, or a combination thereof relative to the amount of palladium present.

14. The method according to claim 1 wherein said chemical additive comprises a halide or hydroxide of lithium.

15. The method according to claim 14 wherein said lithium is present in an amount corresponding to between about 100 equivalents and about 400 equivalents of lithium relative to the amount of palladium present.

16. The method according to claim 1 wherein said chemical additive comprises a halide or hydroxide of magnesium.

17. The method according to claim 16 wherein said chemical additive is present in an amount corresponding to between 25 equivalents and about 150 equivalents of magnesium relative to the amount of palladium present.

18. A method according to claim 1 wherein said base is an organic base.

19. A method according to claim 18 wherein said organic base is selected from the group consisting of tertiary amines, quaternary ammonium hydroxides, quaternary phosphonium hydroxides, and mixtures thereof.

20. A method according to claim 19 wherein said organic base comprises tetramethylammonium hydroxide.

21. A method according to claim 18 wherein said organic base comprises at least one tertiary amine hydrate.

22. A method according to claim 18 wherein said organic base comprises at least one trialkylamine hydrate.

23. A method according to claim 22 wherein said trialkylamine hydrate is triethylamine hydrate.

24. A method according to claim 1 wherein said halide source comprises at least one alkali metal or alkaline earth metal halide.

25. A method according to claim 1 wherein said halide source comprises at least one quaternary ammonium or quaternary phosphonium halide.

26. A method according to claim 1 wherein said aromatic hydroxy compound is selected from the group consisting of phenol, p-cresol, o-cresol, m-cresol, 4-fluorophenol, bisphenol A, methyl salicylate, and mixtures thereof.

27. A method for making diphenyl carbonate, said method comprising:
    contacting in a reaction mixture phenol with carbon monoxide and oxygen in the presence of a carbonylation catalyst comprising palladium or a compound thereof, a co-catalyst, a base, a halide source, and a chemical additive for increasing the amount of diaryl carbonate produced per unit of the carbonylation catalyst, said chemical additive comprising a salt of magnesium or lithium, or a combination thereof, said chemical additive being present in an amount corresponding to at least 25 equivalents of lithium, magnesium, or a combination thereof relative to an amount of palladium present in the carbonylation catalyst.

28. A method for making diphenyl carbonate from phenol, said method comprising:
    contacting phenol with a mixture of carbon monoxide and oxygen in the presence of a carbonylation catalyst comprising palladium or a compound thereof, a co-catalyst, a base, a halide source, and a chemical additive for increasing the amount of diphenyl carbonate produced per unit of the carbonylation catalyst, said chemical additive comprising a salt of magnesium or lithium, or a combination thereof, said chemical additive being present in an amount corresponding to at least 25 equivalents of lithium, magnesium, or a combination thereof relative to an amount of palladium present in the carbonylation catalyst, said cocatalyst being present in an amount corresponding to between about 13 and about 45 equivalents relative to the amount of palladium present in the carbonylation catalyst, said contacting being carried out at a pressure in a range between about 1000 and about 1600 psi and at a temperature between about 80 and about 110° C.

* * * * *